United States Patent [19]

Douglas

[11] Patent Number: 5,057,433
[45] Date of Patent: Oct. 15, 1991

[54] INDICATOR ELEMENTS FOR AUTOCLAVES

[75] Inventor: Malcolm F. Douglas, Swansea, Great Britain

[73] Assignee: Minnesota Mining and Manufacturing Company, St. Paul, Minn.

[21] Appl. No.: 619,657

[22] Filed: Nov. 27, 1990

Related U.S. Application Data

[63] Continuation of Ser. No. 160,649, Feb. 26, 1988, abandoned.

[30] Foreign Application Priority Data

Feb. 27, 1988 [GB] United Kingdom ............... 8704680

[51] Int. Cl.$^5$ ............................................. G01N 31/22
[52] U.S. Cl. ............................................. 436/1; 422/56; 422/57; 422/58; 422/119
[58] Field of Search ............... 463/1; 422/56–58, 422/119

[56] References Cited

U.S. PATENT DOCUMENTS

| | | |
|---|---|---|
| 2,889,799 | 1/1955 | Korpman ............................. 116/114 |
| 3,360,337 | 12/1967 | Edenbaum et al. |
| 3,360,338 | 12/1967 | Edenbaum . |
| 3,360,339 | 12/1967 | Edenbaum . |
| 3,523,011 | 8/1970 | Bhiwandker et al. ............. 436/1 X |
| 3,981,683 | 9/1976 | Larsson ................................ 422/57 |
| 4,168,779 | 9/1979 | Yokokoji et al. .................. 206/439 |
| 4,240,926 | 12/1980 | McNeely ............................ 436/1 X |
| 4,857,450 | 8/1989 | Burrows et al. .................... 430/603 |

FOREIGN PATENT DOCUMENTS

| | | |
|---|---|---|
| 1335076 | 7/1963 | France . |
| 135156 | 4/1979 | German Democratic Rep. ..... 436/1 |
| 1132334 | 10/1968 | United Kingdom . |
| 1211603 | 11/1970 | United Kingdom . |
| 1458553 | 12/1976 | United Kingdom . |
| 2143322 A | 2/1985 | United Kingdom . |

OTHER PUBLICATIONS

Chemical Abstracts, vol. 93, 1980, p. 97, No. 206328s, Columbus, Ohio, U.S. Lead Chemicals, p. 257, Lead Thiosulfate, International Lead Zinc Research Organization, Inc. New York N.Y.

Primary Examiner—Jill Johnston
Attorney, Agent, or Firm—Walter N. Kirn; Jennie G. Boeder

[57] ABSTRACT

An indicator element which provides a visual indication when subjected to correct steam sterilization conditions in an autoclave, the element comprising a substrate having coated thereon an ink formulation comprising as the primary visual change component: (i) a sulfur-containing compound capable of decomposition to yield a metal sulfide under steam sterilization conditions, or (ii) the precursors of which a sulfur-containing compound which will yield said sulfur-containing compound under aqueous conditions.

13 Claims, No Drawings

INDICATOR ELEMENTS FOR AUTOCLAVES

This is a continuation of application Ser. No. 160,149 filed Feb. 26, 1988, now abandoned.

FIELD OF INVENTION

The present invention relates to colour change indicator elements and in particular to colour change indicator elements which effect a colour change under sterilization conditions of high temperature and humidity effected during steam sterilization.

BACKGROUND OF THE INVENTION

In hospitals, clinics and the like, it is standard practice to sterilize various products such as gowns, drapes, sheets, dressings, and other articles, prior to use by placing them in an autoclave where they are subjected to steam sterilization. This practice is necessary to avoid infection and prevent contamination from the use of such articles where the same are not in a sterile condition and it is particularly important where the articles have previously been used in the care of other patients. As there is no visual way of determining whether a particular article is sterile or not it has been the practice to use, with the article, when placed in the autoclave, a colour change indicator element which changes colour under the sterilizing conditions of the autoclave, thus indicating that the particular article or package has been passed through the sterilizing cycle. The indicator may be in the form of a ribbon or card to which a colour change ink has been applied.

It is generally the practice in sterilizing such articles to gather several articles together, bundling the same in a porous wrap, and then the package, held together by tying with string or by pressure-sensitive adhesive tape, is placed in an autoclave together with a sterilizing indicator element, the sterilization indicator element may be either inserted in or applied to the package. Where pressure-sensitive adhesive tapes are used for this purpose, it is convenient to have the colour change indicator on the tape backing. By observation of the visible back of the tape which holds the package together, one can readily determine by its colour change whether or not the same has been passed through the sterilization cycle. Pressure-sensitive adhesive tapes of this type are, for example, described in U.S Pat. No. 2,889,799.

Typical sterilization conditions comprise subjecting the articles to saturated steam at a temperature of between 132° C. and 140° C., usually between 134° C. and 140° C. for a period of not less than 3 minutes. Another steam sterilization cycle comprises subjecting articles to 121° C. for not less than 15 minutes. In order to ensure correct sterilizing conditions, the steam must penetrate unhindered to the centre of the load. This can be achieved only if all of the air is first removed from the sterilizer vessel and its load and this is accomplished typically by a process of evacuation and steam flushing of the sterilizing vessel and its load.

Failure to remove all of the air or the subsequent leakage of air into an evacuated chamber, or the introduction of air or non-condensible gases in the steam supply, causes gas pockets to remain within the porous load, usually in the inner regions thereof. In this case the temperature within the load might be lower in some places than that required during all or part of the sterilization process.

A standard test for the efficiency of air removal and/or the inclusion of non-condensible gases in autoclaves is known as the Bowie/Dick towel test. This test utilises a stack of standard linen Huckaback towels measuring some 270 mm high and about 300 mm ×200 mm in plan. At about the vertical centre of the stack there is placed a sheet of paper bearing so-called autoclave tape or other indicator which undergoes a change in appearance in the presence of certain levels of moisture and temperature. The test pack is processed in the autoclave and the satisfactory result would show an even change in appearance across the whole of the indicator sheet, whereas the presence of air or non-condensible gas in the stack is indicated by a failure of the indicator to change its appearance in certain areas, usually at the centre. This test must be carried out daily before the autoclave is used for the production of sterile porous loads.

There are certain disadvantages associated with this known test. For example, the standard towel stack is too large to fit into many small-chambered autoclaves. Furthermore, the Huckaback towels are expensive and usually require to be laundered at least once a week. The towels require to be aired carefully between tests and they deteriorate gradually and become unusable within about 12 months of normal use. This is because the fibrous consistency becomes matted so that steam cannot readily diffuse through it, thus increasing the risk of misleading test results. Furthermore, Huckaback towels, being made from natural fibre, can give rise to exothermic reactions, i.e. they will absorb moisture very readily with the release of heat, when they are too dry. In the case of the Bowie/Dick test such a phenomenon can result in the temperature within the pack being higher than the temperature in the autoclave chamber and again this can lead to misleading results.

British Patent Specification No. 2143322A discloses a test kit for detecting the presence of air in a steam sterilizer which comprises a first porous mass of at least substantially man-made material, a second porous mass of a similar material, an indicator adapted to undergo a visual change under moist heat sterilising conditions and sandwiched between the masses thus to be in intimate contact therewith, and means for removably holding the masses and indicator in close superimposed relationship, said means being permeable to allow the free passage of air and steam to the external surfaces of said masses.

The test kit is generally in the form of a cuboid having a side dimension in the region of 12 to 15 cm and the indicator may conveniently comprise an autoclave tape or printed sheet having indicator in the shape of a St. Andrews cross or other pattern extending from side to side.

Experimental work has demonstrated that such a device as described is capable of detecting the presence of air in an autoclave. It is also clear from temperature measurements made within the device that the presence of air leads to a lower temperature at the centre of the test pack similar to that observed with the Huckaback towel pack used in the conventional Bowie/Dick test. The presence of air in the autoclave results in uneven change in the indicator, often incomplete colour change towards the centre of the device.

One of the most commonly used colour change media for use as an indicator contains sulfur and lead oxide. The sulfur in the presence of the lead oxide, under the conditions of the steam sterilization, changes from a yellow to a black colour as it is converted to lead sulfide. It has been the practice to mix the sulfur and the lead oxide together in equivalent molar proportions in an ink base which is then applied to an indicator card or to a back of a pressure-sensitive adhesive tape, which, in turn, is then associated with the articles to be sterilized. If the autoclave or other steam sterilizing equipment used is not functioning, or if the package to be sterilized inadvertently gets omitted from being placed in the autoclave, this can readily be determined by the fact that no reaction has occurred between the sulfur and the lead oxide as shown by the lack of colour change in the indicator. Similarly if air or non-condensible gas is present in the autoclave an incomplete reaction will occur in some areas resulting in incomplete generation of the black colour.

One difficulty with such inks is the tendency to stain when in contact with many articles. Staining can be the result of the transfer and reaction of sulfur as the formation of soluble materials during the colour change reaction staining causes unsightly marks on sheets and other articles which may prevent their use. Staining can be reduced by the provision of an overcoat over the printed ink requiring an extra processing step in the production of indicator elements thereby increasing the cost.

Another difficulty with the conventional sulfur lead oxide colour change inks is that they are relatively unstable, necessitating the practice of forming separate solutions of the sulfur and the lead oxide and then combining the two together just prior to using the ink for marking. This is apparently due to the fact that the sulfur and lead oxide tend to react while in the solvent medium used in forming the ink. If the ink solution is prepared several days prior to its use, a substantial reduction in colour change sensitivity results.

Where the colour change indicator is to be used in combination with a pressure-sensitive adhesive tape, as by printing the ink on the back of the tape, the inks containing the sulfur have the further disadvantage that the sulfur in the marking tends to migrate into the pressure-sensitive adhesive where the tape is wound on itself in roll form, thus further reducing the sensitivity of the marking to colour change, when the tape, which the ink marking thereon, is later exposed to steam sterilization conditions.

Although giving a good colour change from a light yellow to a deep black with fresh inks, the colour change indicator markings made from the active ingredients, lead oxide and sulfur, tend to lose much of their sensitivity over extended periods of storage. This is believed to be due to the oxidation of sulfur and is particularly prevalent under relatively hot conditions. Markings may not turn to the same deep black on being subjected to sterilizing conditions but tend to assume a dark grey appearance, with the result that the colour change is not nearly as marked as with fresh inks. This is particularly disadvantageous when the indicators are being used in testing the performance of an autoclave utilising the Bowie/Dick or similar test as misleading results may be obtained.

Despite these inherent disadvantages in colour change media using sulfur and lead oxide, such markings have continued to be widely used as steam sterilization indicators.

British Patent Specification No. 1211603 discloses an indicator material for determining whether steam sterilization has been applied comprising a mixture of lead carbonate and calcium sulfide. In the presence of steam at a temperature of about 120° C. the calcium sulfide decomposes to form calcium hydroxide and hydrogen sulfide. The hydrogen sulfide in turn attacks lead carbonate to form black lead sulfide and carbonic acid.

Other known colour change indicators for indicating steam sterilization include e.g. the use of copper sulfite disclosed in U.S. Pat. No. 3 360 339, which provides a colour change from red to green under steam sterilization conditions, and have not found commercial favour.

It has now been found that there are a number of sulfur-containing compounds which will decompose to yield a sulfide under steam sterilization conditions with a marked colour change.

SUMMARY OF THE INVENTION

According to the present invention there is provided an indicator comprising a substrate having coated thereon a formulation capable of undergoing a visual change upon being subjected to steam sterilization and which undergoes no visible change or a different visible change upon being subjected to conditions milder that steam sterilization, the formulation comprising as the primary visual change component: (i) a sulfur-containing compound capable of decomposition to yield a metal sulfide under steam sterilization conditions or, (ii) the precursors of such a sulfur-containing compound which will yield said sulfur-containing compound under aqueous conditions.

Also according to the invention there is provided an ink formulation which when printed on a substrate is capable of undergoing a visual change upon being subjected to steam sterilization and which undergoes no visible change or a different visual change upon being subjected to conditions milder than steam sterilization, the formulations comprising a binder and as the primary visual change component (i) a sulfur-containing compound capable of decomposition to yield a metal sulfide under steam sterilization conditions, or, (ii) the precursors of such a sulfur containing compound which will yield said sulfur containing compound under aqueous conditions.

It has been found that there are a number of compounds having sulfur-containing radicals which will decompose to the metal sulfide under steam sterilization conditions with a pronounced colour change. Metal sulfides tend to be strongly coloured and are often the most stable form of metal sulfur-containing compounds. Furthermore, they are often insoluble in water and may be held in a binder to prevent staining. The preferred sulfur-containing radical is thiosulfate although other groups may be employed e.g. polythionates etc. Compounds for use as the primary colour change component include:

lead thiosulfate which is white in colour and decomposes to yield black lead sulfide under steam sterilization conditions, copper thiosulfate which is yellow in colour and decomposes to yield black copper sulfide under steam sterilization conditions, ferrous thiosulfate which is light green in colour and decomposes to yield a black sulfide under steam sterilization conditions, nickel thiosulfate which is light green in colour and decomposes to black/green nickel sulfide under steam sterilization conditions, cobalt thiosulfate which is light red/purple in colour and decomposes to deep purple/black cobalt sulfide under steam sterilization conditions, bismuth thiosulfate which is orange/brown in colour and decomposes to black bismuth sulfide under steam sterilization conditions, chromium thiosulfate which is grey/blue in colour and decomposes to dark green chromium sulfide under steam sterilization conditions, silver thiosulfate which is brown in colour and decomposes to black silver sulfide under steam sterilization conditions.

It is also possible to employ precursors of such sulfur-containing compounds which will yield the sulfur-containing compounds under aqueous conditions. For example lead carbonate and sodium thiosulfate may be employed as the colour change component in the ink, these compounds undergoing a double decomposition reaction to yield lead thiosulfate under aqueous conditions. During the steam sterilization cycle lead thiosulfate is initially formed which then decomposes to lead sulfide providing the desired colour change.

The sulfur containing compounds or their precursors used in the invention may be employed as the sole colour change component and may be combined with a binder and solvent in an ink formulation. Such ink formulations may be readily prepared and tend to be physically and chemically stable on storage since the sulfur-containing compounds are stable at ambient temperature. The sulfur-containing compounds may also be used in combination with other components which aid or modify the colour generation under steam sterilization conditions. Other additives include carbonates, particularly lithium carbonate and magnesium carbonate. Such compounds may be used in formulation in amounts up to that of the lead thiosulfate. The selection of these materials is dependent upon the particular property required by the indicator tape. For example, it may be desirable to provide an indicator tape which will not undergo a substantial visual change unless it has been subjected to steam sterilization conditions for a certain period of time, e.g. two minutes.

The binder system for the ink formulations may comprise a film-forming carrier which is permeable to steam in order to obtain a satisfactory colour change under steam sterilization conditions. Binder systems based on nitrocellulose have been found to be particularly effective but many other binder systems may be used e.g. binder systems cured by ultraviolet irradiation or electron beam bombardment e.g. urethane-acrylates, epoxyacrylates and polyester acrylates. Other binder systems include vinyl resins e.g. copolymers of polyvinyl chloride and polyvinyl acetate as disclosed in U.S. Pat. No. 3360339.

The printing ink formulations ma contain other additives, e.g. solvents, defoamers, flow aids and other printing aids.

The formulations are prepared by admixing the components of the binder system, solvent and colour change chemistry, e.g. in a mixer, ball mill or attriter. The binder system generally comprises from 50 to 98% by weight of the ink formulation and the colour change chemistry from 2 to 50% by weight of the ink formulation, usually in the range 20 to 35% by weight of the ink formulation.

A preferred ink formulation of the invention comprises

|  | general range % by weight | preferred % by weight |
| --- | --- | --- |
| lead thiosulfate | 10 to 50 | 29 |
| magnesium carbonate | 0 to 10 | 1 |
| n-propanol | 0 to 30 | 10 |
| n-propyl acetate | 0 to 30 | 14 |
| nitrocellulose binder | 20 to 90 | 45 |

The indicators of the invention may comprise any substrate which is capable of withstanding steam sterilization conditions, i.e. a temperature of 121 to 138° C. in the presence of steam for a period of up to 30 minutes. Suitable substrates include paper which may be absorbent or saturated with a rubber/resin solution or a natural or synthetic latex, coated paper, card, plastics material, metallised material, metal foil and non-woven or woven textile materials.

In one preferred form, the substrate is in the form of a tape, more preferably a pressure sensitive adhesive tape having a release coating upon one surface and a pressure sensitive adhesive on the other such that the tape may be wound in the form of a roll.

A second preferred form comprises a rectangular or square test sheet having an area on which the indicator has been applied of a side dimension in the range 10 to 15 cm for use in a Bowie/Dick test or Lantor cube of the type disclosed in British Patent Specification No. 2143322A.

A particularly preferred form for use with the Lantor cube (commercially available from 3M UK PLC) comprises a paper sheet 30 cm by 15 cm, one half of the sheet having the indicator ink printed thereon (eg. in a pattern comprising a cross formed by diagonal lines extending from two corners and a series of chevrons formed of lines parallel to the cross) and the second half bearing printed matter for recording details of the test, e.g. date, hospital, machine number, test results etc. The indicator paper is folded in half and placed between th blocks of the Lantor cube during testing.

Other substrates may be in the form of a bag or other wrapping in which case the printing ink formulation may be confined to small areas.

The ink formulations may be printed by a range of printing techniques, e.g. flexografic, rotogravure and screen printing, etc. The ink is generally applied in the form of patterns, e.g. stripes, chevrons, etc., in order to provide a visual contrast between areas of the indicator which will provide a visual change after steam sterilization and background areas of the indicator. However, the use of patterns is not essential and the indicator may be completely coated, e.g. by a web coating technique.

The invention will now be illustrated by the following Examples.

EXAMPLE 1

PREPARATION OF LEAD THIOSULFATE

Concentrated nitric acid was added to distilled water to form a dilute solution. Lead carbonate was added slowly and the $CO_2$ effervescence allowed to die down before more was added. Lead carbonate was continually added until no more effervescence was observed. This indicated that a near neutral solution of lead nitrate was obtained. A solution of sodium thiosulfate was made up and when all of the crystals had dissolved, this solution was poured into the solution of lead nitrate. Immediately a white precipitate of lead thiosulfate was formed. It was allowed to settle, the liquor poured off and fresh distilled water was stirred in, the lead thiosulfate allowed to settle and the liquor again poured off. This washing process was again repeated. The slurry was then filtered through a Buchner funnel, the precipitate washed with more distilled water and then ethanol. Finally a wash with diethyl ether was made and the air pulled through the lead thiosulfate by the vacuum to dry off the ether.

EXAMPLE 2

Three stock ink formulations were made up to the following formulation, which ingredients are expressed as parts by weight:

| Ingredient/Ink | A | B | C |
| --- | --- | --- | --- |
| lead thiosulfate | 180 | 270 | 360 |
| n-propanol (solvent) | 103 | 103 | 103 |
| n-propylacetate (solvent) | 155.5 | 155.5 | 155.5 |
| nitrocellulose binder | 476 | 476 | 476 |
| Modaflow | 3.1 | 3.1 | 3.1 |
| Byke 141 | 1.6 | 1.6 | 1.6 |

The nitrocellulose binder used is commercially available from Fishburn Inks, Watford, England and is approximately 30% solids.

Modaflow is a trade mark for a flow aid commercially available from Monsanto.

Byke 141 is a trade mark for a defoamer commercially available from Byke-Chemie GmbH, Wesel, Germany.

The two solvents were added to the container of a laboratory air driven mixer, the mixer started and the lead thiosulfate added slowly. When this had evenly dispersed the binder was slowly poured in followed by the Modaflow and the Byke 141. The ink was then mixed for 20 minutes before use.

Each of the three inks was printed onto 80 gsm photocopy paper using a gravure foil, and dried at a temperature of 50° C.

Inks A1, B1 and C1 were prepared from inks A, B and C above by the addition of magnesium carbonate to each of the formulations in an amount of 12 parts by weight. Each of the inks A1, B1 and C1 were printed as described above.

Inks A2, B2 and C2 were prepared from inks A, B and C above by the addition of magnesium carbonate to each of the formulations in an amount of 24 parts by weight. Each of the inks A2, B2 and C2 were printed as described above.

Printed samples obtained with each of the ink formulations above were placed in a Lantor cube which was placed in an autoclave and subjected to steam sterilization for 3 minutes at 134° C.

The Lantor cube comprised two fibrous blocks essentially made of spun bonded polypropylene-sheets layered one upon another and held together in intimate contact by means of a porous shrink wrap film, said fibrous blocks being 15 cm by 15 cm by 7.5 cm. The two fibrous blocks are held together in intimate contact with the desired indicator between by means of a stainless steel clamp assembly which comprises two square end plates and two side panels which act as compression springs. The Lantor cube and clamp assembly are commercially available from 3M UK PLC.

In each case the printed samples exhibited a clear colour change from white to black and no staining of the cube took place. The clearest and darkest samples were those printed with formulations A2, B1 and B2.

Printed samples using inks B1 and B2 were placed in a Lantor cube and subjected to autoclaving as described above with the exception that air was deliberately introduced into the autoclave in an amount sufficient to provide a temperature difference of 0.5° C. between the drain and the centre of the Lantor cube. This experiment was designed to represent a faulty autoclave having an air leak. The resulting samples exhibited full colour change at the edges of the sheet with areas of incomplete colour change towards the centre thus indicating incomplete sterilization conditions.

EXAMPLE 3

The following ink formulation was prepared

| copper thiosulfate | 300 g |
| --- | --- |
| magnesium carbonate | 12 g |
| n-propanol | 103 g |
| n-propyl acetate | 156 g |
| nitrocellulose binder | 476 g |
| Modaflow | 3.1 g |
| Byke 141 | 1.6 g |
| Total | 1051.7 g |

The ink was made exactly as described previously and printed as before onto photocopy paper. Testing entailed placing a 150 mm square sample into the Lantor cube and subjecting to steam sterilization at 134° C. for 3 minutes.

It was noted that copper thiosulfate is apparently slightly unstable. When initially made it was a canary yellow colour, but when printed it was a yellow-light olive green colour which turns into a dense-black colour on autoclaving in the Lantor cube.

EXAMPLE 4

LEAD NITRATE AND SODIUM THIOSULFATE AS THE COLOUR CHANGE COMPONENTS IN AN AUTOCLAVE INK

An autoclave ink of the following formulation was made by milling all of the components in a ball mill for about 16 hours.

| Lead nitrate | 312 g |
| --- | --- |
| Sodium thiosulfate | 233 g |
| Magnesium Carbonate | 12 g |
| Nitrocellulose binder | 476 g |
| n-propanol | 103 g |
| n-propyl acetate | 156 g |
| Modaflow | 3.1 g |
| Byke 141 | 1.6 g |

The ink was printed onto 80 gsm photocopy paper as previously described and then subjected to development in an autoclave for three minutes at 134° C. with a sample of the sheet in a Lantor cube and in a stack of Huckaback towels as used for a Bowie and Dick test.

A clear colour change from white to black was observed in each sample.

EXAMPLE 5

EVALUATION OF ELEMENTAL THIOSULFATES PRIMARY COMPONENT FOR VISUAL CHANGE INDICATING MEDIUM

The following materials were each weighed out as indicated and dissolved separately in distilled water in a test tube. A number of other test tubes containing 5g of sodium thiosulfate in distilled water were prepared. When the materials were totally in solution the thiosulfate was poured in turn until each of the other solutions to form the respective elemental thiosulfate, either in solution or as a precipitate. Bismuth thiosulfate was precipitated washed and dried to an orange/light brown powder.

Each solution was then boiled for a few minutes and the colour changed observed. Results are indicated in the following Table. In the case of bismuth thiosulfate, the solid was added to a test tube with some distilled water and was then boiled as before.

| MATERIAL | QUANTITY g | COLOUR/PRECIPITATE WITH SODIUM THIOSULFATE | COLOUR/PRECIPITATE WITH BOILING |
| --- | --- | --- | --- |
| Cerous nitrate | 5.83 | milky white | yellow precipitate |
| Caesium chloride | 8.78 | water white | water white |
| Cobaltous nitrate | 5.86 | light red/purple | deep purple/black |
| Bismuth nitrate | 9.77 | orange/brown precipitate | black precipitate |
| Stannous chloride | 4.55 | yellow/white | yellow/white |
| Barium nitrate | 5.26 | white precipitate | off white precipitate |
| Manganous chloride | 3.98 | water white | milky solution |
| Chromium nitrate | 5.37 | grey/blue (milky) | dark green |
| Nickel nitrate | 5.86 | light green | black/green |
| Ferrous sulfate | 5.6 | light green | black |
| Silver nitrate | 6.84 | brown precipitate | black precipitate |

It can be seen from the Table that cobalt, bismuth, chromium, nickel, ferrous and silver thiosulfates provide a pronounced visual change and could be useful in an indicator ink system. The precursors of these compounds may also be used as a colour change component in indicator inks.

EXAMPLE 6

LEAD TETRATHIONATE AS COLOUR CHANGE COMPONENT N AN AUTOCLAVE INK

Sodium thiosulfate solution was slowly added to a solution of blue capricnitrate trihydrate until the blue colour just disappeared. A solution of lead nitrate was then added to give an off-white precipitate of lead tetrathionate. The precipitate was allowed to settle, the liquor poured off and distilled water added with stirring. The precipitate was filtered, washed again with distilled water, methylated spirits and finally with ether and thereafter dried.

50g of the lead tetrathionate was dispersed in 100g of the nitrocellulose binder used in Example 2 and the composition was hand spread onto sheets of 80gsm photocopy paper using No. 1 and No. 8 K Bars. The sheets were dried for 5 minutes at 50° C. and then autoclaved for 3 minutes at 134° C. All samples developed a dark black colour.

I claim:

1. A steam sterilization indicating ink formulation which when printed on a substrate is capable of undergoing a visual change upon being subjected to steam sterilization and which undergoes no visible change or a different visual change upon being subjected to conditions milder than steam sterilization, the formulation comprising a non-reactive binder and as the primary visual change component:
   (i) a sulfur-containing compound which is not a sulfide at ambient conditions but is capable of decomposition to yield a metal sulfide under steam sterilization conditions or,
   (ii) a precursor of a sulfur-containing compound, which sulfur-containing compound is not a sulfide at ambient conditions but is capable of decomposition to yield a metal sulfide under steam sterilization conditions, said precursor capable of yielding said sulfur-containing compound under aqueous conditions.

2. A steam sterilization indicating ink formulation which when printed on a substrate is capable of undergoing a visual change upon being subjected to steam sterilization and which undergoes no visible change or a different visual change upon being subject to conditions milder than steam sterilization, the formulation comprising a non-reactive binder and as the primary visual change component, a sulfur-containing compound which is not a sulfide at ambient conditions, but is capable of decomposition to yield a metal sulfide under steam sterilization conditions.

3. The ink formation of claim 1 wherein said visual change component comprises said precursor of said sulfur-containing compound, and said precursor comprises lead carbonate and sodium thiosulfate.

4. The ink formation of claim 1 wherein said visual change component comprises a sulfur-containing compound and said full sulfur-containing compound comprises a thiosulfate or polythiosulfate radical.

5. The ink formation of claim 1 wherein said visual change component comprises a sulfur-containing compound and said sulfur-containing compound is a thiosulfate selected from the group consisting of lead thiosulfate selected from the group consisting of lead thiosulfate, copper thiosulfate, silver thiosulfate, bismuth thiosulfate, cobalt thiosulfate, chromium thiosulfate, nickel thiosulfate and ferrous thiosulfate.

6. The ink formation of claim 1 wherein said visual change component comprises said precursor of said sulfur-containing compound and said precursor comprises lead nitrate and sodium thiosulfate.

7. The ink formation of claim 1 wherein said binder comprises nitrocellulose.

8. The ink formulation of claim 1 wherein said visual change component comprises a sulfur-containing compound and said sulfur-containing compound comprises lead thiosulfate present in a concentration of between about 10 and 50 percent by weight of said ink formulation and said binder comprises a nitrocellulose binder present in a concentration of between about 20 and 90 percent by weight of said ink formulation; and wherein said ink formulation further comprises magnesium carbonate in a concentration of between about 0 and 10 percent by weight of said ink formation, n-propanol in a concentration of between and 0 and 30 percent by weight of said ink formation and n-propyl acetate in a concentration of between about 0 and 30 percent by weight of said ink formation.

9. The ink formation of calim 8 wherein said lead thiosulfate is present in a concentration of about 29 percent by weight of said ink formulation, said magnesium carbonate is present in a concentration of about 1 percent by weight of said ink formulation, said n-propanol is present in a concentration of about 10 percent by weight of said ink formation, said n-propyl acetate is present in a concentration of about 1 percent by weight of said ink formulation, and said nitrocellulose binder is present in a concentration of about 45 percent by weight of said in formulation.

10. A steam sterilization indicator comprising a substrate having coated on at least a portion of one major exterior surface thereof a medium capable of undergoing a visual change upon being subjected to steam sterilization and which undergoes no visible change or a different visible change upon being subjected to conditions milder than steam sterilization, wherein said medium comprises as the primary visual change component:

(i) a sulfur-containing compound which is not a sulfide at ambient conditions, but is capable of decomposition to yield a metal sulfide under steam sterilization conditions or,
   (ii) a precursor of a sulfur-containing compound, which sulfur-containing compound is not a sulfide at ambient conditions but is capable of decomposition to yield a metal sulfide under steam sterilization conditions, said precursor capable of yielding said sulfur-containing compound under aqueous conditions.

11. The indicator of claim 10 wherein said medium comprises as the primary visual change component said precursor of said sulfur-containing compound, which precursor comprises lead carbonate and sodium thiosulfate.

12. The indicator of claim 10 wherein said substrate is selected from paper, saturated or coated paper, card, plastics material, metallized material, metal foil, woven textile materials or non-woven textile materials.

13. The indicator of claim 10 wherein said medium is overcoated with a release coating and the opposite major surface of said substrate is coated with a pressure sensitive adhesive.

* * * * *

UNITED STATES PATENT AND TRADEMARK OFFICE
CERTIFICATE OF CORRECTION

PATENT NO. : 5,057,433

DATED : October 15, 1991

INVENTOR(S) : Malcolm F. Douglas

It is certified that error appears in the above-identified patent and that said Letters Patent is hereby corrected as shown below:

Abstract, line 8, "which" should read --such--.

Col. 1, line 4, "160,149" should read --160,649--.

Col. 10, line 48, delete "full".

Col. 10, lines 54-55, delete "selected from the group consisting of lead thiosulfate".

Col. 11, line 21, "in" should read --ink--.

Signed and Sealed this

Thirteenth Day of April, 1993

Attest:

STEPHEN G. KUNIN

Attesting Officer

Acting Commissioner of Patents and Trademarks